(12) United States Patent
Koerperick et al.

(10) Patent No.: US 9,404,072 B2
(45) Date of Patent: Aug. 2, 2016

(54) NEAR-INFRARED OPTICAL INTERFACES FOR DISPOSABLE BIOPROCESSING VESSELS

(71) Applicant: ASL Analytical, Inc., Coralville, IA (US)

(72) Inventors: Edwin John Koerperick, North Liberty, IA (US); Jonathon Todd Olesberg, Iowa City, IA (US); Christine Esther Evans, North Liberty, IA (US); Mark Allen Arnold, Iowa City, IA (US); Gary Wray Small, Coralville, IA (US)

(73) Assignee: ASL Analytical, Inc., Coralville, IA (US)

( * ) Notice: Subject to any disclaimer, the term of this patent is extended or adjusted under 35 U.S.C. 154(b) by 0 days.

(21) Appl. No.: 14/709,932

(22) Filed: May 12, 2015

(65) Prior Publication Data

US 2015/0330903 A1 Nov. 19, 2015

Related U.S. Application Data

(60) Provisional application No. 61/992,735, filed on May 13, 2014.

(51) Int. Cl.
| | | |
|---|---|---|
| *G02B 6/00* | (2006.01) | |
| *C12M 1/00* | (2006.01) | |
| *G01N 21/75* | (2006.01) | |
| *C12M 1/34* | (2006.01) | |
| *G01N 21/17* | (2006.01) | |
| *G01N 21/01* | (2006.01) | |
| *B01L 9/00* | (2006.01) | |
| *C12Q 1/02* | (2006.01) | |
| *G01N 15/14* | (2006.01) | |
| *G01N 21/359* | (2014.01) | |
| *G01N 15/06* | (2006.01) | |
| *G01N 21/03* | (2006.01) | |
| *G01N 15/00* | (2006.01) | |

(52) U.S. Cl.
CPC .. *C12M 1/00* (2013.01); *B01L 9/00* (2013.01); *C12M 1/34* (2013.01); *C12M 23/28* (2013.01); *C12M 41/00* (2013.01); *C12M 41/46* (2013.01); *C12Q 1/02* (2013.01); *G01N 15/06* (2013.01); *G01N 15/1456* (2013.01); *G01N 21/01* (2013.01); *G01N 21/0303* (2013.01); *G01N 21/17* (2013.01); *G01N 21/359* (2013.01); *G01N 21/75* (2013.01); *G01N 2015/0053* (2013.01); *G01N 2015/0065* (2013.01); *G01N 2015/0693* (2013.01); *G01N 2021/0307* (2013.01); *G01N 2021/0321* (2013.01); *G01N 2021/0378* (2013.01)

(58) Field of Classification Search
USPC .............................................. 385/12
See application file for complete search history.

(56) References Cited

U.S. PATENT DOCUMENTS

| | | | |
|---|---|---|---|
| 6,388,750 B1 * | 5/2002 | Liu ........................ | G01F 23/292 356/246 |
| 6,488,892 B1 * | 12/2002 | Burton .................... | B01L 9/523 356/244 |
| 6,494,613 B2 | 12/2002 | Terentiev | |

(Continued)

*Primary Examiner* — Sung Pak (57) ABSTRACT

An optical sampling apparatus for disposable flexible bioprocessing vessels includes features for optical interrogation of the vessel contents by means of transmission or transflection spectroscopy. This optical interrogation allows for the determination of quantities and parameters of substances in fluids contained within the vessels during bioprocesses.

30 Claims, 5 Drawing Sheets

(56) References Cited

U.S. PATENT DOCUMENTS

| | | | |
|---|---|---|---|
| 6,542,231 B1 * | 4/2003 | Garrett | G01N 21/05 250/227.11 |
| 7,218,810 B2 * | 5/2007 | Hillendahl | G01N 21/253 356/246 |
| 7,379,783 B2 | 5/2008 | Popp | |
| 7,379,784 B2 | 5/2008 | Popp | |
| 7,392,107 B2 | 6/2008 | Popp | |
| 7,799,273 B2 | 9/2010 | Popp | |
| 7,824,902 B2 | 11/2010 | Selker et al. | |
| 8,008,065 B2 | 8/2011 | Selker et al. | |
| 8,491,839 B2 | 7/2013 | Popp | |
| 8,550,439 B2 | 10/2013 | Terentiev et al. | |
| 8,591,811 B2 | 11/2013 | Popp | |
| 8,660,680 B2 | 2/2014 | Popp | |
| 8,817,259 B2 | 8/2014 | Schick et al. | |
| 9,008,815 B2 | 4/2015 | Popp | |
| 9,092,028 B2 | 7/2015 | Popp | |
| 9,195,228 B2 | 11/2015 | Popp | |
| 2003/0207331 A1 * | 11/2003 | Wilson, Jr. | B01J 19/0046 435/7.1 |
| 2004/0038390 A1 * | 2/2004 | Boege | B01L 7/52 435/288.7 |
| 2005/0265905 A1 * | 12/2005 | Young | B01J 19/0046 422/129 |
| 2006/0139632 A1 * | 6/2006 | Gerner | G01N 21/05 356/246 |
| 2007/0231223 A1 * | 10/2007 | Young | B01J 19/0046 422/187 |
| 2015/0037445 A1 * | 2/2015 | Murphy | B29C 67/0088 425/131.1 |
| 2015/0345689 A1 * | 12/2015 | Selker | F16L 58/185 435/289.1 |

* cited by examiner

NEAR-INFRARED OPTICAL INTERFACES FOR DISPOSABLE BIOPROCESSING VESSELS

CROSS-REFERENCE TO RELATED APPLICATIONS

This application claims the benefit of U.S. provisional patent application No. 61/992,735, filed May 13, 2014, for "Optical Interfaces for Bioprocessing Vessels." Such application is incorporated herein by reference in its entirety.

BACKGROUND

The present invention relates to optical sampling means for providing optical communication between an optical instrument and a disposable vessel of flexible polymeric construction for applications including, but not limited to, pharmaceutical, food processing, and chemical manufacturing as well as other laboratory and industrial processes.

The use of optical and electronic instrumentation to monitor and control the contents of vessels and changes taking place therein is well known in the art. Processing and storage of, for example, food, beverage, chemical, agricultural, fuel, and pharmaceutical products have historically taken place primarily in multiple-use vessels comprised of stainless steel and/or glass. Numerous hardware approaches enabling interrogation and analysis of the contents of such vessels by, for example, optical, electronic, and electrochemical techniques have been described in the art. Dissolved oxygen may be measured by, for example, electrochemical probes with oxygen-permeable membranes, as well as fluorescent sensor techniques. Measurement of pH is possible by electrochemical techniques as well as fluorescent methods. Probes for measurement of optical characteristics of materials in rigid vessels by transmission, reflection, and attenuated total reflection (ATR) are also known in the art. Such probes are often of tubular form and primarily metal construction, protruding through a head plate or side wall of a vessel and into the fluid under process. Probes and sensors of this general description are commonly designed for robustness and longevity—tolerating use, cleaning, and often sterilization for many process cycles. Such multiple-use probes and sensors typically have form factors that are not accommodating to interfacing with single-use bioreactors, particularly flexible bioreactors and those with small working volumes. Flexible bioreactors, also known as bag bioreactors, lack rigidity—surfaces commonly distort during operation, making attachment and positioning of typical multiple-use probes difficult and unstable. Bioreactors with small working volumes simply do not have the surface area or volume to support many of the sensors and probes that are common in the art. Moreover, such prior art sensors and probes do not commonly fit within the model of single-use technology as they are not disposable and must be in contact with the process fluid, thereby requiring the cleaning, sterilization, and aseptic insertion steps that single-use technology seeks to avoid.

Regular cleaning and maintenance of multiple-use vessels is required to maintain process integrity, and sterile conditions are often necessary, demanding yet more laborious and/or costly cleaning and sterilization procedures. The maintenance, cleaning, and disinfection of multiple-use process vessels coupled with the high initial cost of the equipment has led to accelerating adoption of single-use, disposable vessels in multiple industries. These single-use vessels are most commonly constructed of polymers, and are often purchased pre-sterilized such that the user may immediately put them to use. As such, sensors that will come into contact with the fluid are commonly integrated into the vessel before sterilization and sterilized with the vessel. Any sensors or connections to the vessel that are not integrated and sterilized with the vessel may be externally sterilized and installed via aseptic ports. While use of sensors or probes that are not installed into the vessel prior to sterilization of the vessel is feasible, it is typically undesirable due to the additional labor required of the end user as well as the increased probability of contamination. Such single-use vessels offer several additional benefits over conventional multiple-use bioreactors: ease of use; reduced setup labor for end users; significantly reduced cleanup time; and lower equipment costs. Single-use disposable bioreactors are available in a variety of sizes and form factors—working volumes range from sub-milliliter to thousands of liters.

A key aspect in bioprocessing is being able to transition processes from small-scale experiments in the research lab to a large-scale production environment. The research and effort to transition from small-scale experiments to production is known as scale-up, and this process is commonly challenging and time consuming. Scale-up often comprises three major phases—the research phase where initial studies are performed and processes are selected and verified; the pilot plant phase where processes are further studied, refined, and verified in higher volume processes; and the production phase where large-scale manufacturing is performed. The conditions present in small-volume research bioreactors may be markedly different from those present in the larger bioreactors in the pilot plant and on the production floor. Indeed, processes can vary considerably even between different bioreactors in the research lab. In order to execute the scale-up process in the most efficient manner possible, it is desirable to have the ability to optimize a plurality of process parameters and constituent concentrations, and often to be able to control such parameters and constituent concentrations. Ideally such monitoring and control capabilities will be uniform throughout the various stages of scale-up. Bioreactors having working volumes of microliters to few milliliters are commonly known as micro-bioreactors, and are often configured such that multiple micro-bioreactors are used to perform experiments in parallel. Such multiplexed experiments with cell culture or fermentation processes enable evaluation of process conditions, cell lines, or other variables in an efficient manner. So-called miniature-bioreactors commonly have working volumes of tens to few hundreds of milliliters, and may offer another step in the scale-up process. Similarly to micro-bioreactors, mini-bioreactors are often configured in groups for parallel experimentation, though with a working volume that better represents more standard process conditions. While reliable monitoring of constituent concentrations of fluids in bioprocesses such as nutrient concentrations remains challenging even in large-volume bioreactors, the challenge is amplified with micro- and mini-bioreactors given the space constraints and form factors. Sensor technologies capable of providing such constituent concentration information, and ideally control of such concentrations, in bioreactors used across the product development arc from research lab to production plant are desired in the biotechnology and pharmaceutical industries.

Sensors for measurement of a variety of parameters within single-use vessels have been demonstrated. For example, analysis of physical and chemical conditions such as pH and dissolved oxygen (DO) is possible by means of sensors comprising fluorescent dots within the bioreactor fluid. Single-use and disposable temperature and pressure sensors have been demonstrated. Optical interfaces for vessels of polymeric construction, which may be single-use and/or flexible vessels, are also known in the art, though to a far lesser extent than similar interfaces for multiple-use vessels. Interfaces for transmission, reflection, and ATR optical measurements have been disclosed, however these interfaces and ports are generally not optimized for near-infrared spectroscopic applications. Numerous polymers are available that are at least partially transparent to visible and short-wave infrared (SWIR), though these polymers are often substantially opaque or exhibit significant absorption structure at wavelengths longer than 1.5 µm.

Bioreactors commonly require frequent monitoring and strict control in order to ensure optimal environmental and nutritional conditions for fermentation, cell cultures, or similar processes contained therein. While sensors are available to continuously measure parameters such as DO and pH as is hardware and software to control these parameters, sensors and systems to monitor nutrients and other constituents in an automated fashion and control the levels thereof have historically been largely absent in the art. This is the case for both multiple- and single-use bioreactors, however sensor solutions to interface with single-use bioreactors have been particularly lacking.

Measurement of fluid constituents by spectroscopic methods, particularly infrared spectroscopic methods, presents a robust means to monitor said constituents and control levels thereof within bioreactors and process vessels in general. In order to optically interface with polymeric vessels and their contents, especially those with flexible walls, integrated and robust optical interface solutions are desired. These solutions may be substantially transparent in the wavelength range of interest, and offer high measurement stability and optical throughput. The requirement of material transparency is particularly challenging for infrared spectroscopy, principally near- and mid-infrared spectroscopy, where optical absorption by many commonly used polymers is unacceptably high when polymer thicknesses are within the satisfactory range to maintain mechanical integrity. When in an optical spectroscopic configuration, embodiments of optical sensors where the path or sample length through the vessel contents is variable and controlled may be desirable for some applications. Embodiments where any optical elements that are to come in contact with the vessel contents are fused to the vessel and sterilized with the vessel are often preferable to solutions where optical monitoring components are inserted aseptically subsequent to sterilization.

BRIEF SUMMARY

As used herein, the terms "optical" and "light" refer to electromagnetic radiation having vacuum wavelengths between 300-20,000 nm.

As used herein, "near infrared", "near-infrared", and "NIR" mean the region of the electromagnetic spectrum generally spanning wavenumbers between $3300\,cm^{-1}$ and $14,000\,cm^{-1}$ (corresponding to wavelengths of approximately 0.7 µm to 3.0 µm).

As used herein, "interrogation" and "sampling" mean illuminating a sample with optical radiation and collecting at least a portion of the radiation having interacted with said sample for optical analysis.

As used herein, "constituent" means a chemical analyte, protein, DNA, component in a fluid, cell, or solid suspended in a fluid.

The present invention relates to disposable flanges and probes, generally of polymeric construction, for disposable flexible vessels, comprising features for optical interrogation of fluids contained within such bioprocessing vessels. An optical instrument may be used in conjunction with embodiments of the present invention to determine and/or control quantities of substances in fluids contained within bioprocessing vessels. The invention pertains to optical transmission and transflection measurements in general and particularly to near-infrared spectroscopic measurements.

A plurality of embodiments of optical interfaces for disposable bioprocessing vessels, including vessels with flexible construction, is provided. All embodiments provide elements for optical communication between the fluid contents of a bioprocessing vessel and an optical interface that communicates with an optical instrument. Embodiments are provided where optical interfaces are configured for near-infrared optical spectroscopy, particularly transmission and transflection near-infrared spectroscopy. In one embodiment, an optical probe configured to extend into the contents of a bioprocessing vessel is configured on a flange which may be fusibly, adhesively, or compressively bonded to a flexible bioprocessing vessel. In this embodiment, input and output optical communication elements are located on a single flange fixed to the bioprocessing vessel. Alignment features on the optical probe provide a connection means to an optical interface which may provide optical communication with an optical instrument.

In another embodiment, an optical probe is provided that is configured to be attached to two flanges on a flexible bioprocessing vessel. In this embodiment, electromagnetic radiation is communicated into optical elements on a first flange, and electromagnetic radiation having interacted with fluid contained within the bioprocessing vessel is communicated to a second flange for communication to an optical instrument. Such an embodiment provides for desirable location of an optical sampling region within a bioprocessing vessel, for example away from the wall of the vessel. Such an embodiment also provides for simple optical configurations whereby few optical components may be required while providing advantageously efficient optical throughput.

In yet another embodiment, a disposable flange is provided and comprises optical fibers configured to provide optical communication with the contents of a disposable flexible bioprocessing vessel. In this embodiment, one or more optical waveguides provide optical communication to a recessed optical sampling region whereby electromagnetic radiation may interact with a fluid, and one or more optical waveguides communicate a portion of the electromagnetic radiation having interacted with a fluid to an optical interface for communication with an optical instrument.

The detailed description and drawings provided herein will offer additional scope to certain implementations of the present invention. It should be understood that the described implementations are provided as examples only. Those skilled in the art will recognize that numerous variations and modifications of the described implementations are within the scope of the invention.

DETAILED DESCRIPTION

Figure 1:
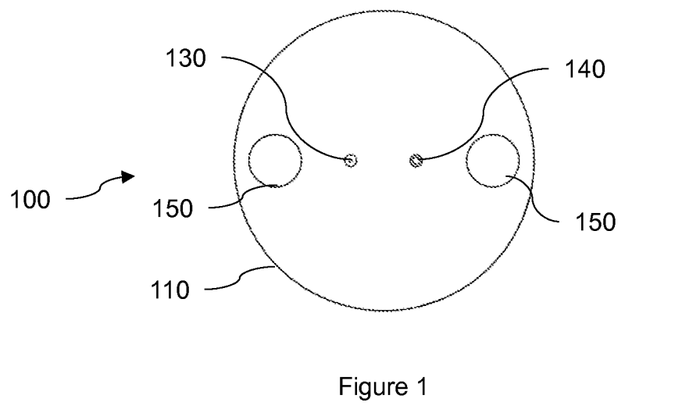
FIG. 1 shows a bottom view of a flange with an integrated optical probe.
Figure 2:
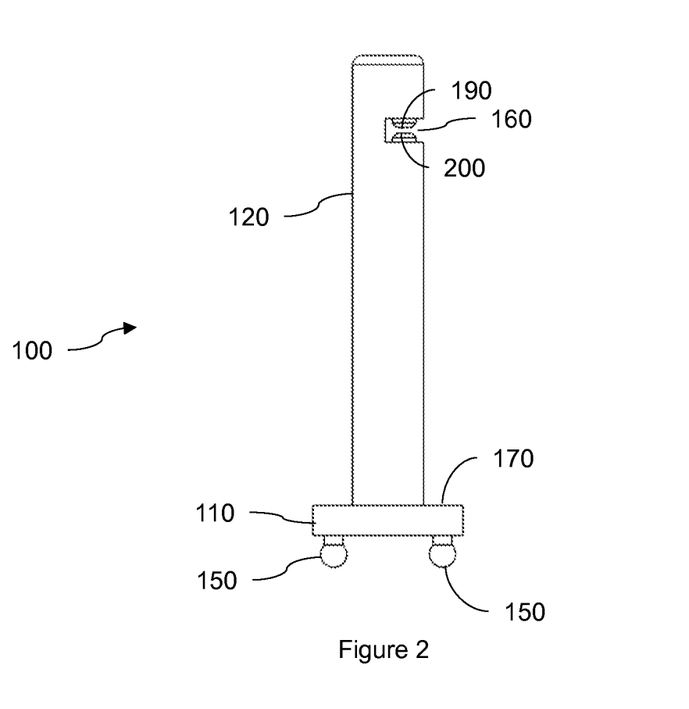
FIG. 2 shows a side view of the flange with integrated optical probe from FIG. 1.

An embodiment of the present invention comprising a disposable flange and integral optical probe is shown in FIG. 1 and FIG. 2. The bottom view of the disposable flange 100 in FIG. 1 shows a rigid polymer base member 110 with a first optical waveguide 130, a second optical waveguide 140, and alignment features 150 for alignment with an optical interface. An optical probe 120 integral to the disposable flange 100 houses the optical waveguides 130 and 140 and optionally additional optical elements to provide optical communication to a fluid within a disposable bioprocessing vessel. All wetted surfaces on the rigid polymer base member 110 and probe 120 will desirably be constructed of materials being FDA and/or USP Class VI compliant to ensure compatibility with bioprocesses. While the interior surface 170 of the rigid polymer base member 110 will desirably be constructed of such compliant materials, features exterior to the bioprocessing vessel and not in contact with the fluid contained therein such as the alignment features 150 need not be constructed from such materials. Materials such as fluorinated ethylene propylene (FEP), polycarbonate, polypropylene, polyetherimide, and polyethylene may be suitable choices for construction of disposable flange 100 components depending on the preferred application and method of sterilization.

Disposable bioprocessing vessels are commonly provided to end users pre-sterilized so that end users may immediately put the products to use. It is also desirable that components and sensors used within disposable bioprocessing vessels to monitor bioprocesses are compatible with sterilization techniques, and that that such components and sensors are sterilized with the vessel. Sterilization of vessels and associated components and sensors together reduces contamination risks by minimizing handling and exposure of the components to non-sterile environments. Materials used for construction of embodiments of the present invention will preferably be amenable to sterilization by one or more of gamma irradiation, beta irradiation, ethylene oxide gas, or autoclave. It is also desirable that materials chosen for construction of embodiments of the present invention will be FDA and/or USP Class VI compliant after sterilization.

The optical probe 120 of the disposable flange 100 comprises an optical sampling region 160 as shown in FIG. 2. The optical sampling region 160 provides for interrogation of a fluid within a disposable bioprocessing vessel by receiving a fluid with which electromagnetic radiation may interact, and communicating at least a portion of the electromagnetic radiation having interacted with the fluid to an optical interface via optical elements such as waveguides. Said optical sampling region comprises at least a first optical surface 190 and a second optical surface 200 between which an optical path length through the fluid is provided. Said first 190 and second 200 optical surfaces may comprise optical elements such as windows or lenses, or may be provided by the ends of the optical waveguides 130 and 140. In the present invention, the length of optical path through the fluid will desirably be between 0.5 mm and 2.0 mm inclusively. This range of optical path lengths is favorable when near-infrared electromagnetic radiation having wavenumbers between 3300 cm-1 and 5600 cm-1 is employed in the optical measurement owing to sufficiently high optical interaction length with the fluid and sufficiently low water absorption.

Due to the fact that many polymers exhibit strong absorption features in certain wavelength ranges of the electromagnetic spectrum, it may be advantageous that any polymers that are within the optical beam path be selected to minimize such absorption. For example in the near-infrared wavelength range of the electromagnetic spectrum, strong absorption features may arise from C—H, C—O, O—H, and N—H chemical bonds. For this reason it may be preferable to use polymers lacking such chemical bonds in the optical sampling regions of disposable bioprocessing vessels designed for optical interrogation by such wavelengths. Perfluorinated polymers such as Teflon® polytetrafluoroethylene (PTFE), ethylene tetrafluoroethylene (ETFE), Teflon® fluorinated ethylene propylene (FEP), Teflon® amorphous fluoroplastics (AF), and Teflon® perfluoroalkoxy copolymer (PFA) lack the listed chemical bonds and thus may be preferable for polymer materials within the optical path. Alternatively, other polymer materials may be used if sufficiently thin to provide adequate optical transmission in the desired wavelength range. For example, polycarbonate being less than 0.25 mm in thickness may offer satisfactory optical transmission in the near-infrared wavelength range.

Alignment features 150 are provided to engage the disposable flange 100 with an optical interface or reader that provides optical communication with an instrument. Said alignment features 150 will preferably maintain alignment of the first 130 and second 140 optical waveguides with corresponding features on an optical interface such that the features remain in register and the optical coupling of the optical interface and disposable flange 100 is stable during bioprocesses. The ability to maintain positioning between the disposable flange 100 and optical interface is of high importance in spectroscopic applications. When an optical instrument is provided to determine the quantities of substances within a fluid, variations in the optical communication between the disposable flange 100 and optical interface may produce undesirable fluctuations in a determined quantity.

Figure 3:
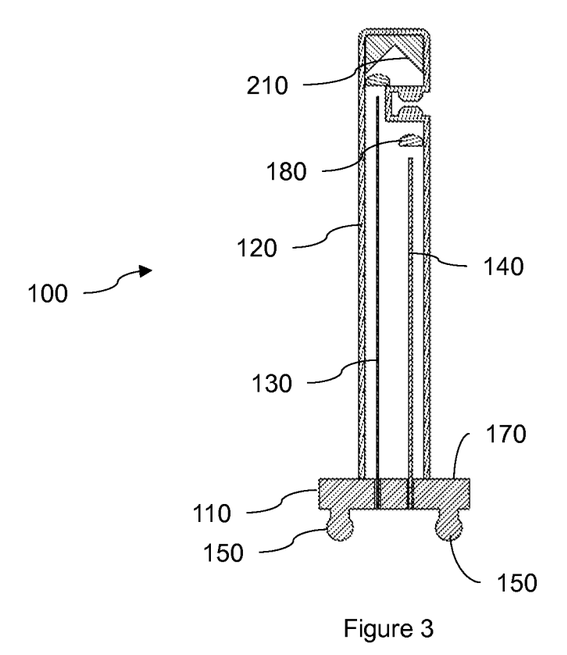
FIG. 3 shows a sectional side view of the flange with integrated optical probe from FIG. 1.

Further detail of the disposable flange 100 with integral optical probe 120 is shown in the side sectional view in FIG. 3. Additional optical elements 180 such as lenses may be used within the probe 120 to increase the optical throughput. A reflector 210 at an end of the probe may be provided to direct the electromagnetic radiation to the optical sampling region 160. Embodiments are also provided where only first optical waveguide 130 and second optical waveguide 140 provide optical communication with the optical sampling region without additional focusing or collection optical elements. For near-infrared measurements, optical waveguides 130 and 140 will preferably be comprised of materials offering low optical absorption in the wavelength range of interest. Optical fibers such as low-OH content silica-clad-silica offer a combination of low cost and acceptable performance over a wide range of near-infrared wavelengths. Such low-OH silica optical fibers offer acceptable optical transmission from the visible region of the electromagnetic spectrum to approximately 4150 cm-1. Lengths of low-OH silica optical fibers may be desirably be kept as short as possible in near-infrared applications to avoid the increasing optical absorption at longer wavelengths. Other optical fiber materials such as indium fluoride (InF$_3$), zirconium fluoride (ZrF$_4$), and chalcogenide glass may offer superior optical performance, though at additional cost. It may be preferable to use a lower cost material such as low-OH silica in disposable components where the length of optical fiber may be minimized to reduce optical absorption, and a higher performance material for optical fibers external to the disposable components and bioprocessing vessel (such as in an optical interface or reader that is configured for multiple uses).

Embodiments of the present invention provide for communication of near-infrared electromagnetic radiation between an optical interface and the optical probe 120 integral to the rigid polymer base member 110. Optical spectroscopy with near-infrared electromagnetic radiation offers a plurality of advantages for determining quantities of substances in fluids. Optical absorption features in the near-infrared are often present for substances having C—H, O—H, C—O, N—H, S—H, and P—H chemical bonds, offering the possibility to determine quantities of substances containing such chemical bonds using near-infrared spectroscopy. While water is sufficiently strongly absorbing in several wavelength ranges throughout the infrared electromagnetic spectrum and can limit the effectiveness of transmission or transflection spectroscopic techniques to determine quantities of substances, the 3300 cm$^{-1}$ to 5600 cm$^{-1}$ wavenumber range provides a water transmission window centered at approximately 4600 cm$^{-1}$. In this wavenumber range the water absorption is sufficiently low to allow adequate optical throughput through fluid samples with a sufficiently short optical path length to determine quantities of substances by spectroscopic techniques. In order to provide sufficient optical throughput through a fluid and also provide a satisfactory optical path length for interaction of electromagnetic radiation with the fluid, optical path lengths through fluids ranging from 0.5 mm to 2.0 mm are preferable for embodiments of the present invention. Measurements with near-infrared spectroscopic techniques may be used to determine quantities of substances in fluids such as alcohols, sugars, lipids, organic acids, peptides, and steroidal molecules as such substances often comprise optical absorption features at near-infrared wavelengths due to their chemical bonds. In addition to measurements of optical absorption by transmission or transflection measurement approaches to determine quantities of substances by their absorption spectra, near-infrared spectroscopic techniques may be used to determine parameters such as cell density, cell viability, or turbidity. Due to the reduction in optical scattering with increasing wavelength, optical path lengths between 0.5 mm and 2.0 mm may be used even when conducting high cell density bioprocesses such as Pichia pastoris fermentations.

Embodiments of the present invention may be provided for determining quantities of substances in a plurality of stages of bioprocessing. It is often desirable to perform monitoring of quantities of substances within fluids during several stages of bioprocessing. Monitoring during static stages such as product storage may be used for example to determine whether a product is stable. Monitoring during dynamic stages such as a growth or product formation stage may be used to track the quantities of substances in fluids as a function of time and also to enable control of the quantities of substances. For example, carbon sources may be monitored during a growth stage and feedback control used to maintain desired levels of one or more of such carbon sources. The present invention provides configurations for determining quantities of substances in fluids during storage, growth, product formation, product purification, and product formulation stages. Embodiments of the present invention may provide for processes such as batch processes as well as continuous processes such as perfusion processes. Downstream processes such as product purification may also utilize embodiments of the present invention for determination of constituents in fluids.

Figure 4:
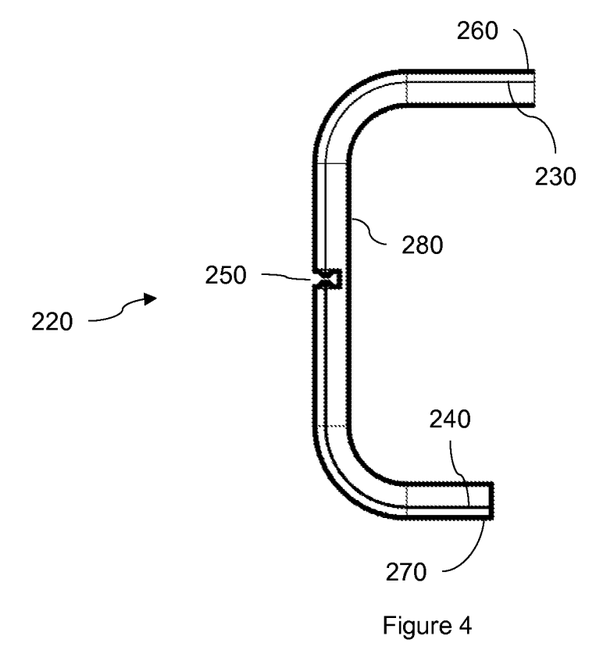
FIG. 4 shows a sectional side view of an optical probe configured to be installed between two flanges on a bioprocessing vessel.
Figure 5:
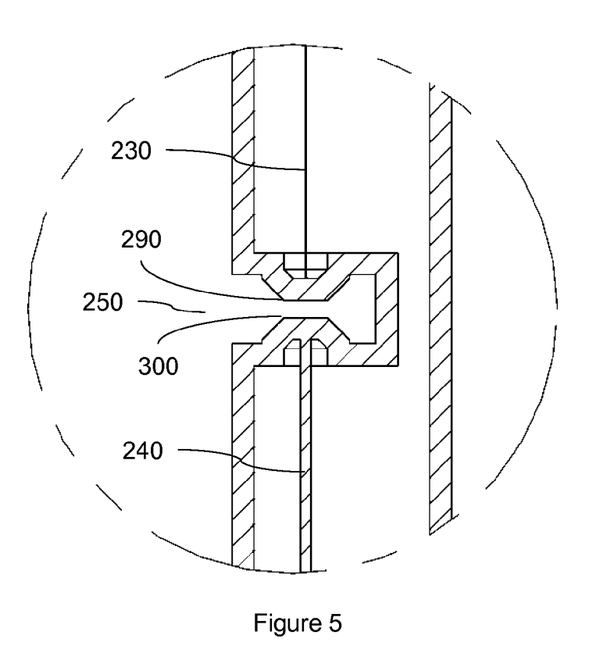
FIG. 5 shows a detailed sectional view of the optical sampling region of the optical probe in FIG. 4.

In another embodiment, an optical probe is provided that is configured to be attached to two separate flanges on a disposable flexible bioprocessing vessel. In this embodiment, a first flange is configured with a first optical waveguide, and a second flange is configured with a second optical waveguide. A sectional side view of a disposable optical probe configured to be positioned between two flanges is shown in FIG. 4. In this embodiment, the optical probe 220 comprises a first end 260 having a first optical waveguide 230 and second end 270 having a second optical waveguide 240. Said first end 260 and second end 270 comprise a polymer support member 280 and are configured to be integrated with separate flanges on a disposable flexible bioprocessing vessel. A recessed region providing an optical sampling region 250 is provided whereby optical communication is provided between a fluid and said first 230 and second 240 optical waveguides. A more detailed sectional view of the optical probe 220 of FIG. 4 is shown in FIG. 5. The optical sampling region 250 comprises a first surface 290 in optical communication with the first optical waveguide 230 and a second surface 300 in optical communication with the second optical waveguide 240 whereby an optical path length is formed between the first surface 290 and second surface 300. The optical path length may be chosen to suit a variety of applications—for near-infrared spectroscopic applications the optical path length through a fluid is desirably between 0.5 mm and 2.0 mm inclusively. Communication of electromagnetic radiation from the first optical waveguide 230 to the first surface 290, through the optical sampling region 250 providing an optical path length, and subsequently providing a portion of electromagnetic radiation having interacted with a fluid to the second surface 300 and second optical waveguide 240 provides an optical transmission measurement geometry.

Figure 6:
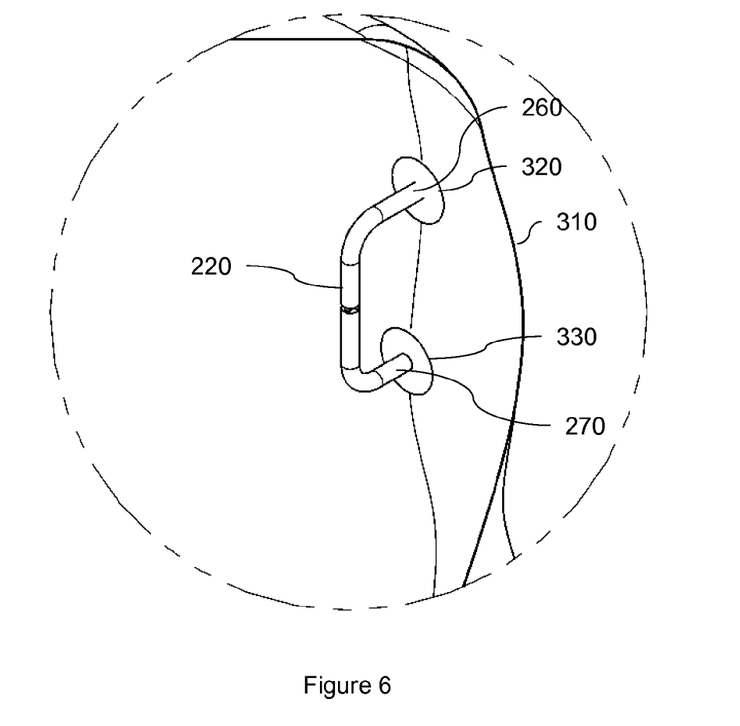
FIG. 6 shows a cutaway view of a bioprocessing vessel with the optical probe from FIG. 4 installed.

A cutaway view of the optical probe 220 installed within a flexible bioprocessing vessel 310 is shown in FIG. 6. A first polymer flange 320 is attached to the first end 260 of the optical probe 220 and a second polymer flange 330 is attached to the second end 270 of the optical probe 220. The flanges 320 and 330 and optical probe 220 may be positioned advantageously in a bioprocessing vessel 310 for example to avoid other internal components or position the optical sampling region 250 in a desirable location for fluid sampling. The optical sampling region 250 will preferably be positioned away from gas sparging equipment and in a location with adequate mixing and fluid flow in order to avoid entrapment of gas bubbles within the optical sampling region 250. An advantage of the present invention is that the optical sampling region 250 may be placed in a plurality of locations within a bioprocessing vessel 310 and need not be confined to the periphery of the vessel.

In the embodiment shown in FIG. 6 the first optical waveguide 230 is attached to a first polymer flange 320 and the second optical waveguide 240 is attached to a second polymer flange 330, the need for steering optics to direct the electromagnetic radiation back towards the origin optical elements is eliminated. Additionally, if the length of optical path in the optical sampling region 250 is sufficiently small, preferably less than or equal to 2.0 mm, the need for focusing and collection optical elements such as lenses may be eliminated. In the embodiment shown in FIG. 4 and FIG. 5, the first optical waveguide 230 has a smaller diameter than the second optical waveguide 240 so that the second optical waveguide 240 can collect a substantial portion of the electromagnetic radiation having exited the first optical waveguide 230. As an exemplary case, if a first optical waveguide 230 comprising an optical fiber with a core diameter of 100 µm is used in conjunction with a second optical waveguide 240 comprising an optical fiber having a core diameter of 600 µm, the length of optical path between the ends of the fibers is 1.0 mm and a numerical aperture of 0.22 for the optical fibers is assumed, a coupling efficiency between the optical fibers of greater than 80% may be achieved in an aqueous solution (losses due to Fresnel reflections are not accounted for in this efficiency figure). In such implementations involving optical fibers, it is desirable that the minimum bend radius of the optical fibers not be exceeded. Bending the optical fibers beyond the minimum bend radius may lead to optical losses and instability in the electromagnetic radiation delivered to an optical instrument. The polymer support member 280 housing the optical fibers may comprise both flexible and rigid portions, and will desirably be configured such that it is bend-limiting in that any enclosed optical fibers may not be bent beyond the minimum bend radii. The polymer support member 280 will desirably comprise at least a rigid portion near the optical sampling region 250 such that expected perturbations to the optical probe 220 during normal use do not cause fluctuations in the optical path length.

Embodiments of the present invention also provide for optical probes comprising more than one pair of optical waveguides, or where a single set of optical waveguides is configured to communicate more than one wavelength range of electromagnetic radiation. A plurality of wavelength ranges of the electromagnetic spectrum may be utilized to perform measurements on fluid samples, and the present invention optical probe may provide for interrogating fluid samples with more than one wavelength range. As an example of providing multiple wavelength regions in a single pair of optical waveguides, low-OH silica optical fibers may be used to communicate both near-infrared electromagnetic radiation and a separate wavelength range of electromagnetic radiation simultaneously. Alternatively, a second pair of optical waveguides may be provided that have favorable transmission properties for the second wavelength range of interest.

An exemplary case of where two wavelength ranges of electromagnetic radiation may be useful would be in low cell density cell cultivation process. For example, near infrared electromagnetic radiation may be used for the determination of quantities of substances within a fluid sample in a disposable bioprocessing vessel. Examples of such substances include alcohols, sugars, lipids, proteins, organic acids, peptides, and steroidal molecules. Due to higher optical scattering, measurements at shorter wavelengths can be used to quantitate cell density. For example, wavelengths significantly shorter than NIR, near 600 nm, are often used to measure cell density. Measurement of cell density in combination with nutrient quantitation throughout a bioprocess is often desirable as this information can yield key insights into the progress of a bioprocess.

Figure 7:
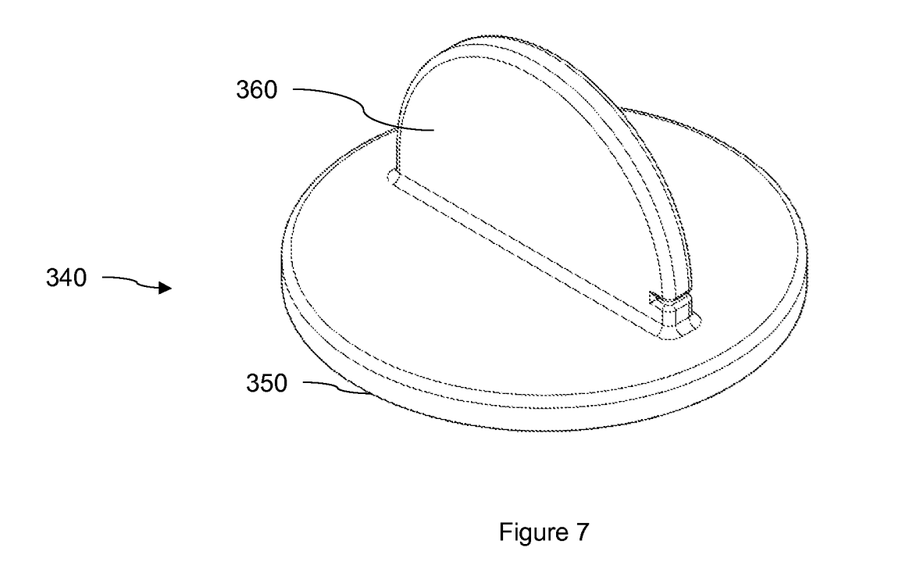
FIG. 7 shows an isometric view of a flange with integrated optical waveguides.
Figure 8:
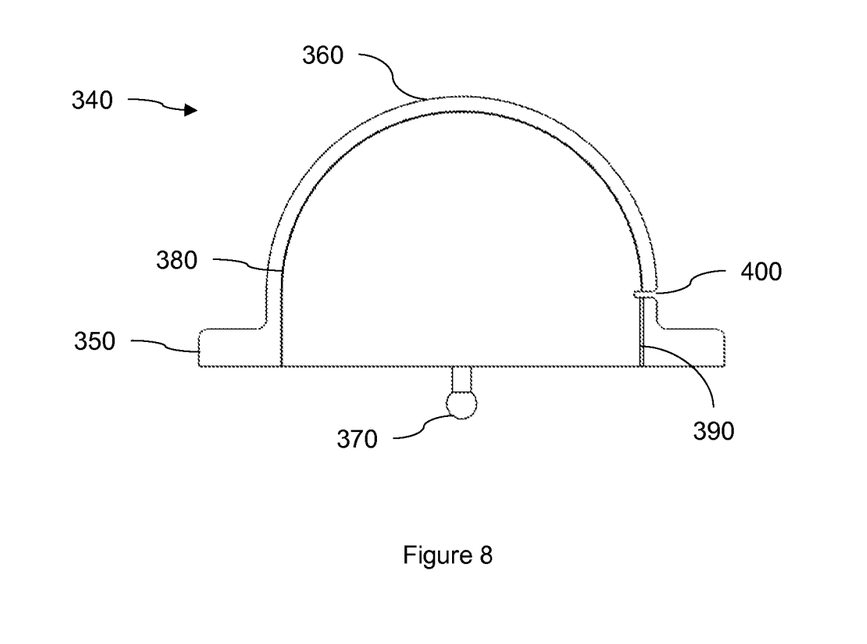
FIG. 8 shows a sectional side view of the flange with integrated optical waveguides from FIG. 7.
Figure 9:
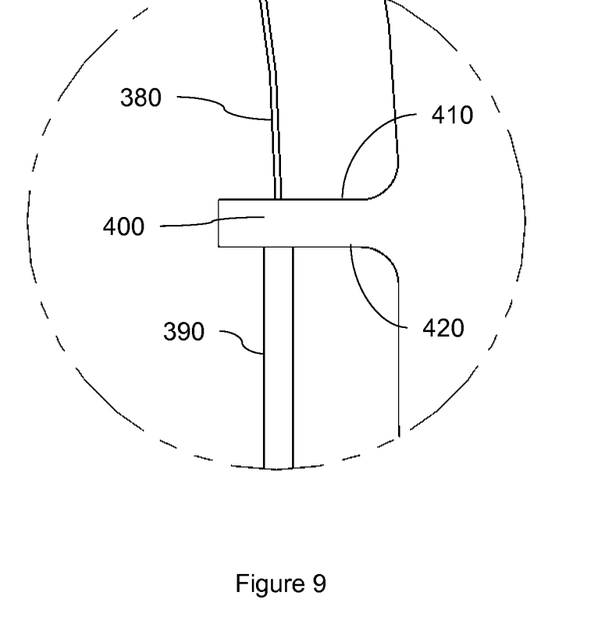
FIG. 9 shows a detailed sectional view of the flange with integrated optical waveguides from FIG. 7.

In yet another embodiment of the present invention, a disposable flange comprising integral optical waveguides is provided. The isometric view in FIG. 7 shows one embodiment of the disposable flange 340. A polymer base member 350 and support structure 360 comprise the main external features, and alignment features 370 are provided for engagement with an optical interface that provides optical communication with the disposable flange 340 and an optical instrument. As shown in the sectional view in FIG. 8, a first optical waveguide 380 is provided to communicate electromagnetic radiation to a recessed region 400 for optical sampling, and a second optical waveguide 390 is configured to collect and communicate a portion of the electromagnetic radiation having interacted with a fluid sample in the recessed region 400 to an optical instrument. The sectional view in FIG. 9 provides additional detail about the elements for optical sampling with the disposable flange 340. A recessed region 400 comprises a first surface 410 in optical communication with the first optical waveguide 380 and a second surface 420 in optical communication with the second optical waveguide 390. The first 410 and second 420 surfaces in optical communication with the first 380 and second 390 optical waveguides provide an optical path length within a fluid sample in the recessed region 400. Certain embodiments of the present invention provide optical path lengths being 0.5 mm to 2.0 mm in length through the fluid, inclusively.

Figure 10:
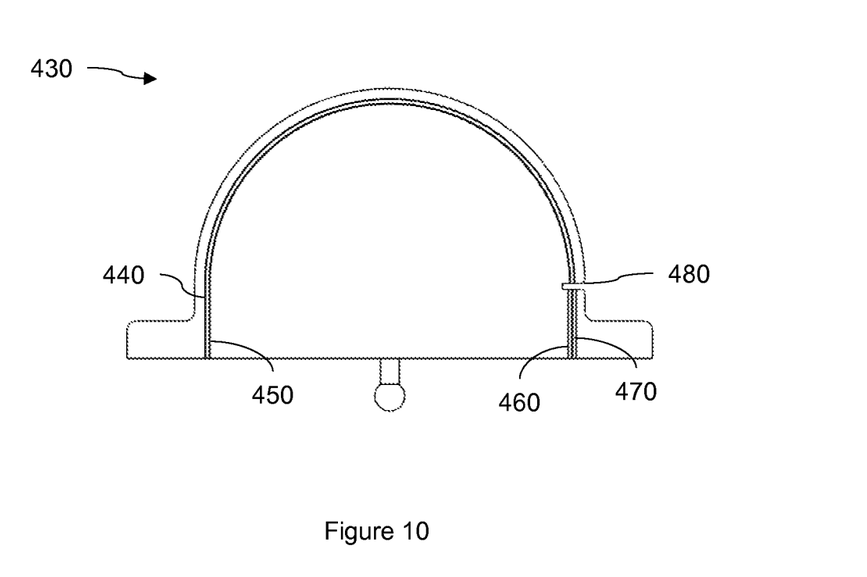
FIG. 10 shows a sectional side view of a flange with two pairs of integrated optical waveguides.

Another embodiment of the present invention is shown in the sectional view in FIG. 10. In this embodiment, a polymer flange 430 comprises two pairs of optical waveguides. A first pair of optical waveguides comprises a first input waveguide 440 and a first output waveguide 470. Said first pair of optical waveguides may be configured to communicate near-infrared electromagnetic radiation between an optical interface and a fluid sample within an optical sampling region 480. A second pair of optical waveguides is also provided comprising a second input optical waveguide 450 and a second output optical waveguide 460. Said second pair of optical waveguides may be configured to communicate electromagnetic radiation in a second wavelength region outside of the near-infrared wavelength range. The recessed optical sampling region 480 may be configured to provide one or more optical path lengths, wherein different path lengths may be provided for different pairs of optical waveguides.

The disposable flanges 340 and 430 are configured to be installed in flexible bioprocessing vessels by fusible bonding, adhesive bonding, or compression. Methods such as thermal or ultrasonic welding may be used to provide a fluid impermeable joint between the flange and disposable vessel. Flanges will desirably be placed within a region of the disposable bioprocessing vessel where the recessed optical sampling regions are fully immersed in the fluid within the bioprocessing vessel and remain immersed throughout the entire bioprocess. Placement away from gas sparging equipment and in a region with satisfactory fluid mixing may be preferable to minimize inclusion and entrapment of gas bubbles.

The present invention has been described with reference to the foregoing specific implementations. These implementations are intended to be exemplary only, and not limiting to the full scope of the present invention. Many variations and modifications are possible in view of the above teachings. The invention is limited only as set forth in the appended claims. All references cited herein are hereby incorporated by reference to the extent not inconsistent with the disclosure herein. Unless explicitly stated otherwise, flows depicted herein do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims. Any disclosure of a range is intended to include a disclosure of all ranges within that range and all individual values within that range.

The invention claimed is:

1. A disposable flange for interrogating a fluid in a disposable bioprocessing vessel, said flange comprising:
   a rigid base member comprising a polymer;
   a disposable optical probe integral to said rigid polymer base member, said optical probe comprising two optical waveguides being at least partially transparent to near-infrared electromagnetic radiation;
an optical sampling region between said two optical waveguides configured to receive the fluid, wherein said optical sampling region provides a length of optical path through said fluid between 0.5 mm and 2.0 mm, inclusive;
a mechanism for aligning an optical interface with said integral optical probe for near infrared optical sampling;
wherein an optical interface is configured to communicate near infrared electromagnetic radiation to and from said integral optical probe.

2. The disposable flange of claim 1, wherein said disposable flange is suitable for sterilization by one or more of gamma irradiation, beta irradiation, ethylene oxide, or autoclave.

3. The disposable flange of claim 1, wherein said disposable flange comprises fluorinated ethylene propylene (FEP).

4. The disposable flange of claim 1, wherein said near-infrared electromagnetic radiation to which the two optical waveguides are transparent comprises wavenumbers between 3300 cm$^{-1}$ and 5600 cm$^{-1}$.

5. The disposable flange of claim 1, wherein said disposable flange is configured for a bioprocess selected from the group consisting of a growth stage, a product formation stage, a purification stage, a storage stage, and a product formulation stage.

6. A disposable flange for interrogating a fluid within a flexible disposable bioprocessing vessel, said flange comprising:
A first optical waveguide and a second optical waveguide;
a polymer base member comprising a support structure to retain and support said first and second optical waveguides and features to align said base member with an optical interface, at least a portion of said polymer base member configured to be in fluid communication with the fluid contained within the disposable bioprocessing vessel;
a recessed region within said polymer base member, said recessed region comprising a first surface being in optical communication with said first optical waveguide and an opposing second surface being in optical communication with said second optical waveguide whereby an optical sampling region having an optical path length is formed between said first and second waveguides;
wherein said first optical waveguide is configured to communicate electromagnetic radiation from an optical interface into said optical sampling region for interaction with a fluid contained therein, and said second optical waveguide is configured to communicate a portion of said electromagnetic radiation having interacted with a fluid to said an optical interface, thereby providing a transmission optical measurement.

7. The disposable flange of claim 6, wherein no further steering or imaging optical elements are included between said first optical waveguide and said second optical waveguide.

8. The disposable flange of claim 6, wherein said polymer base member comprises fluorinated ethylene propylene (FEP).

9. The disposable flange of claim 6, wherein said flange is suitable for sterilization by one or more of gamma irradiation, beta irradiation, ethylene oxide, or autoclave.

10. The disposable flange of claim 6, wherein said optical path length is between 0.5 mm and 2.0 mm inclusively.

11. The disposable flange of claim 6, wherein said optical waveguides comprise optical fibers, and wherein a diameter of said second optical waveguide is greater than a diameter of said first optical waveguide.

12. The disposable flange of claim 6, wherein said first optical waveguide is an optical fiber configured in a curved geometry, and wherein a radius of curvature of said curve is greater than or equal to a minimum bend radius of the fiber.

13. The disposable flange of claim 6, wherein said optical waveguides comprise optical fibers comprising a material selected from the group consisting of low-OH silica, chalcogenide glass, zirconium fluoride ($ZrF_4$), and indium fluoride ($InF_3$).

14. The disposable flange of claim 6, wherein the optical waveguides are configured to communicate near-infrared electromagnetic radiation.

15. The disposable flange of claim 14, wherein said optical waveguides are at least partially transparent to near-infrared electromagnetic radiation comprising wavenumbers between 3300 cm$^{-1}$ and 5600 cm$^{-1}$.

16. The disposable flange of claim 6, wherein said disposable flange is configured for a bioprocess selected from the group consisting of a storage stage, a growth stage, a product formation stage, a purification stage, and a product formulation stage.

17. The disposable flange of claim 14, wherein the optical waveguides are further configured to communicate electromagnetic radiation in a wavelength range outside of near-infrared.

18. The disposable flange of claim 6, further comprising a third optical waveguide and a fourth optical waveguide configured to communicate electromagnetic radiation, wherein said polymer base member further comprises a support structure to retain and support said third and fourth optical waveguides and said first surface is in optical communication with said third optical waveguide and said second surface is in optical communication with said fourth optical waveguide whereby an optical sampling region having a second optical path length is formed between said third and fourth waveguides, and further wherein said third optical waveguide is configured to communicate electromagnetic radiation from the optical interface into said optical sampling region for interaction with a fluid contained therein, and said fourth optical waveguide is configured to communicate a portion of said electromagnetic radiation having interacted with the fluid to said optical interface, thereby providing a transmission optical measurement.

19. The disposable flange of claim 18, wherein the first and second optical waveguides are configured to communicate near-infrared electromagnetic radiation, and said third and fourth optical waveguides are configured to communicate electromagnetic radiation in a wavelength range outside of near-infrared.

20. A disposable optical probe for interrogating a fluid in a flexible disposable bioprocessing vessel, said optical probe comprising:
a first optical waveguide and a second optical waveguide;
a first polymer flange and a second polymer flange located on a disposable bioprocessing vessel;
a polymer support member for housing said first and second optical waveguides, said polymer support member comprising a first end and a second end, wherein said first end is connected to said first polymer flange and said second end is connected to said second polymer flange;
a recessed region within said polymer support member, said recessed region comprising a first surface being in optical communication with said first optical waveguide and an opposing second surface being in optical communication with said second optical waveguide whereby an optical sampling region having an optical path length is formed between said first and second optical waveguides;

wherein said first optical waveguide is configured to communicate electromagnetic radiation from an optical interface into said optical sampling region for interaction with said fluid contained in said disposable bioprocessing vessel, and said second optical waveguide is configured to communicate a portion of said electromagnetic radiation having interacted with said fluid to an optical interface, thereby providing a transmission optical measurement.

21. The disposable optical probe of claim 20, wherein said optical probe and flanges are suitable for sterilization by one or more of gamma irradiation, beta irradiation, ethylene oxide, or autoclave.

22. The disposable optical probe of claim 20, wherein said optical path length is between 0.5 mm and 2.0 mm inclusively.

23. The disposable optical probe of claim 20, wherein said optical waveguides comprise optical fibers, and wherein the diameter of said second optical waveguide is greater than the diameter of said first optical waveguide.

24. The disposable optical probe of claim 20, wherein said optical waveguides comprise optical fibers comprising a material selected from the group consisting of low-OH silica, chalcogenide glass, zirconium fluoride ($ZrF_4$), and indium fluoride ($InF_3$).

25. The disposable optical probe of claim 20, wherein the optical waveguides are configured to communicate near-infrared electromagnetic radiation.

26. The disposable optical probe of claim 25, wherein said optical waveguides are at least partially transparent to near-infrared electromagnetic radiation comprising wavenumbers between 3300 $cm^{-1}$ and 5600 $cm^{-1}$.

27. The disposable optical probe of claim 20, wherein said disposable optical probe is configured for a process selected from the group consisting of a storage stage, a growth stage, a product formation stage, a purification stage, and a product formulation stage.

28. The disposable optical probe of claim 25, wherein the optical waveguides are further configured to communicate electromagnetic radiation in a wavelength range outside of near-infrared.

29. The disposable optical probe of claim 20, further comprising a third optical waveguide and a fourth optical waveguide configured to communicate electromagnetic radiation, wherein said polymer support member houses said third and fourth optical waveguides, said first surface is in optical communication with said third optical waveguide and said second surface is in optical communication with said fourth optical waveguide whereby an optical sampling region having a second optical path length is formed between said third and fourth optical waveguides, and wherein said third optical waveguide is configured to communicate electromagnetic radiation from the optical interface into said optical sampling region for interaction with said fluid contained in said disposable bioprocessing vessel, and said fourth optical waveguide is configured to communicate a portion of said electromagnetic radiation having interacted with said fluid to the optical interface, thereby providing a transmission optical measurement.

30. The disposable optical probe of claim 29, wherein the first and second optical waveguides are configured to communicate near-infrared electromagnetic radiation, and said third and fourth optical waveguides are configured to communicate electromagnetic radiation in a wavelength range outside of the near-infrared.

* * * * *